(12) United States Patent
Mañanas Villanueva et al.

(10) Patent No.: US 10,602,979 B2
(45) Date of Patent: Mar. 31, 2020

(54) METHOD WITH BIOFEEDBACK FOR TRAINING THE MUSCLES OF THE PELVIC FLOOR

(71) Applicants: UNIVERSITAT POLITÈCNICA DE CATALUNYA, Barcelona (ES); HOSPITAL CLÍNIC DE BARCELONA, Barcelona (ES)

(72) Inventors: Miguel Angel Mañanas Villanueva, Barcelona (ES); Juan Jose Ramos Castro, Barcelona (ES); Montserrat Espuña Pons, Barcelona (ES); Amelia Perez Gonzalez, Barcelona (ES)

(73) Assignees: Universitat Politècnica de Catalunya, Barcelona (ES); Hospital Clínic de Barcelona, Barcelona (ES)

( * ) Notice: Subject to any disclaimer, the term of this patent is extended or adjusted under 35 U.S.C. 154(b) by 0 days.

(21) Appl. No.: 14/414,893

(22) PCT Filed: Jul. 16, 2013

(86) PCT No.: PCT/ES2013/070507
§ 371 (c)(1),
(2) Date: Jan. 15, 2015

(87) PCT Pub. No.: WO2014/013118
PCT Pub. Date: Jan. 23, 2014

(65) Prior Publication Data
US 2015/0182161 A1    Jul. 2, 2015

(30) Foreign Application Priority Data
Jul. 16, 2012    (ES) .................................. 201231114

(51) Int. Cl.
*A61B 5/00*    (2006.01)
*A61B 5/0488*    (2006.01)
(Continued)

(52) U.S. Cl.
CPC ............ *A61B 5/486* (2013.01); *A61B 5/0004* (2013.01); *A61B 5/04004* (2013.01);
(Continued)

(58) Field of Classification Search
CPC .............................. A61B 5/486; A62B 23/20
See application file for complete search history.

(56) References Cited

U.S. PATENT DOCUMENTS 5,277,197 A * 1/1994 Church ................. A61B 5/486
                                                      600/546
5,411,548 A * 5/1995 Carman ............ A61B 5/04882
                                                      600/546
(Continued)

FOREIGN PATENT DOCUMENTS

DE           4441267          5/1996
WO       WO 9415667 A1       7/1994

OTHER PUBLICATIONS

Neumann et al. 'Pelvic Floor and Abdominal Muscle Interaction: EMG Activity and Intra-abdominal Pressure' International Urogynecol Journal (Feb. 2002) 13:125-132.*
(Continued)

*Primary Examiner* — Patrick Fernandes
(74) *Attorney, Agent, or Firm* — Robert J. Hess; Hess Patent Law Firm

(57) ABSTRACT

The invention relates to a method with biofeedback for training muscles of the pelvic floor, applicable to the treatment of urinary incontinence, fecal incontinence and prolapse of pelvic organs, using a portable electronic device for capturing, by means of sensors, EMG signals relating to abdominal activity and the area to be treated during muscle exercises, said device providing results visually and/or acoustically, the method comprising: placing a vaginal or rectal sensor (10) and two sensors (11) in the lower abdominal area, performing exercises working the muscles of the
(Continued)

pelvic floor, providing evaluation of the exercises performed and storing results. The user places the sensors herself, the device evaluating the correct placement of the sensors indicating to the user that the suitable position has been reached through said acoustic and/or visual means, and performing a step prior to the exercises for acquiring muscle tone.

8 Claims, 2 Drawing Sheets

(51) Int. Cl.
    *A63B 23/20*     (2006.01)
    *A63B 71/06*     (2006.01)
    *A61B 5/20*     (2006.01)
    *A61B 5/04*     (2006.01)
    *A61B 5/11*     (2006.01)

(52) U.S. Cl.
    CPC ........ *A61B 5/04882* (2013.01); *A61B 5/1107* (2013.01); *A61B 5/202* (2013.01); *A61B 5/6823* (2013.01); *A61B 5/6873* (2013.01); *A61B 5/742* (2013.01); *A61B 5/7405* (2013.01); *A63B 23/20* (2013.01); *A63B 71/0622* (2013.01); *A63B 2071/0625* (2013.01); *A63B 2230/605* (2013.01)

(56) References Cited

U.S. PATENT DOCUMENTS

| | | | |
|---|---|---|---|
| 5,423,329 A * | 6/1995 | Ergas | A61B 5/486 600/546 |
| 5,881,731 A | 3/1999 | Remes | |
| 6,264,582 B1 * | 7/2001 | Remes | A63B 23/20 482/8 |
| 7,979,110 B1 * | 7/2011 | Krzypow | A61B 5/04025 600/509 |
| 2004/0015096 A1 * | 1/2004 | Mok | A61B 5/0002 600/547 |
| 2005/0113703 A1 * | 5/2005 | Farringdon | A61B 5/0428 600/509 |
| 2010/0185114 A1 * | 7/2010 | Lillegard | A61B 5/0402 600/544 |

OTHER PUBLICATIONS

Lorenzo Gome, MF; Silva Abuin, JM; Garcia Criado, FJ; Geanini Yaguez, A; Urrutia Avisrror, M. "Tratamiento de la incontinencia urinaria de esfuerzo con Biofeedback perineal con electrodos de superficie", Actas Urológicas Espanolas, 2008.

* cited by examiner

METHOD WITH BIOFEEDBACK FOR TRAINING THE MUSCLES OF THE PELVIC FLOOR

FIELD OF THE INVENTION

The present invention relates to a method with biofeedback envisaged for training muscles of the pelvic floor, applicable to the treatment of urinary incontinence, fecal incontinence and prolapse of pelvic organs, in which an electronic device associated with sensors (generally electrodes) is used for capturing and processing EMG signals relating to an area to be treated and to abdominal activity, showing a user or patient some graphs or images representative of the results of the captured and processed signals through visual and/or acoustic display means, which can possibly be replaced with a computer screen.

It is well known that performing periodic muscle exercises of a muscle area to be treated such as the indicated area (i.e., the pelvic floor), capturing information about the muscle activity of the area involved while performing exercises leads to improvement in most cases for strengthening muscles or improving the sensitivity of said exercised area.

The invention therefore falls within non-invasive methods for treating dysfunctions such as urinary or fecal incontinence, through muscle exercises controlled by an electronic device prepared for capturing, through feedback by means of sensors, electromyographic EMG signals relating to the pelvic floor and EMG signals relating to a lower abdominal area, simultaneously showing a user information illustrating the muscle activity of the treated area, and auxiliary messages particularly offering guidance for said exercises, by means of a visual and/or acoustic interface, while the user performs said muscle exercises.

The invention particularly proposes a method which makes it easier for the user herself to learn and perform the mentioned exercises after a simple training step with the help of a medical practitioner, with the capacity to automatically adapt the parameters of said exercises to the particular conditions of each user at all times throughout the period of performing the exercises and optimizing result capturing and processing.

Throughout this description the term "user", or subject of the method, shall refer to a female user, although it is clear that the method would also be applicable to male users in the case of fecal incontinence.

BACKGROUND OF THE INVENTION

Patent document U.S. Pat. No. 5,277,197 discloses a microprocessor-controlled system for performing unsupervised training exercises, with EMG feedback, in which it describes the use of an electromyographic sensor producing a signal representative of an EMG activity (electromyographic signal the electric source of which is the potential of the muscle membrane), said sensor being an electrode that is positioned adjacent to a muscle group to be controlled and describes a chain of elements for converting and carrying said signal to a display screen where the level of muscle activity generated by the user is shown so that the user can perform variable contraction and relaxation exercises in response to the results detected by the mentioned electromyographic sensor.

Patent document U.S. Pat. No. 5,423,329 describes in detail a non-invasive method of treatment for urinary incontinence, envisaged to be performed by medical personnel in which sensors are applied for controlling muscles of the anus and other sensors are applied under and on the thigh and in the lower abdomen area, acquiring information from said several sources to provide supervision information (measurements from a base reference to a peak reference) resulting from voluntary contractions by the patient aided by practitioners.

Patent document U.S. Pat. No. 5,881,731 describes a vaginal probe-type device in which the particularity of pelvic floor asymmetry has been envisaged and sensors have been envisaged for such purpose on both sides of a tubular portion that can be inserted into the vagina, such that when the device is suitably positioned, it can acquire information from the muscles of the two sides, separately.

The method of the invention uses means for capturing pelvic floor muscle activity data, such as those mentioned, but proposes and allows using same at home, i.e., applied by a user without the help of any medical personnel, except in one or more initiation sessions, integrating said pelvic floor muscle activity data and displaying to the user, which not only allows the user to perform suitable exercises, but also allows evaluating them and dynamically adapting same both to the conditions for performing specific exercises (number of exercises or time in which they are performed, in particular after an earlier workout) and to the individual characteristics of the users every time they perform exercises.

BRIEF DESCRIPTION OF THE INVENTION

To achieve said objectives, the invention proposes a method with biofeedback for training muscles of the pelvic floor, applicable to the treatment of urinary or fecal incontinence, in which an electronic device is used for capturing, through sensors, EMG signals relating to a vaginal or anal area while performing muscle exercises, and EMG signals relating to abdominal activity, showing a representation associated with said processed EMG signals, providing information about the result of said exercises, through visual and/or acoustic display means, which can possibly be replaced with a computer screen with which said electronic device is associated.

The method is based on processes and/or techniques which have already been used, generally with medical support, comprising the following steps:

a) placing a vaginal or rectal sensor in the user's vagina or rectum;
b) placing at least two sensors in a lower abdominal area;
c) performing a repetitive series of exercises working the muscles of the pelvic floor or adjacent areas,
d) providing evaluation of the exercises performed by means of acoustic signals and/or on a screen; and
e) storing the results of each session The exercises of step c) include two types: rapid and sustained or resistance contraction exercises for training the different types of muscle fibers.

The method according to this invention is characterized in that it is performed by the user herself who will place said vaginal or rectal sensor as well as said sensors in the lower abdominal area.

Likewise, a portable electronic device that can be located in an area close to the area where exercises are performed will be at the user's disposal and said electronic device captures information from said vaginal or rectal sensor and from said sensors in the abdominal area by means of radiofrequency or another type of wireless signal.

To that end, the method of the invention comprises step b1) after step b) and before step c) for performing said repetitive series of exercises which comprises verifying suitable placement (sufficient EMG signal capture) of said at least two sensors for the lower abdominal area, indicating to the user that a suitable position of the sensors has been reached through said acoustic and/or visual means.

The proposed method is also characterized by performing before step c) first relaxation exercises for establishing a baseline level of muscle activity which is established from the muscle tone captured by the EMG signal provided by said abdominal sensors and vaginal or rectal sensors, and obtaining a maximum level, requesting to that end maximum contraction of said areas from said user.

Other features of the invention will become apparent after reading an example of application that will be provided in detail in reference to the drawings depicting the equipment used.

DETAILED DESCRIPTION OF THE INVENTION

Figure 1:
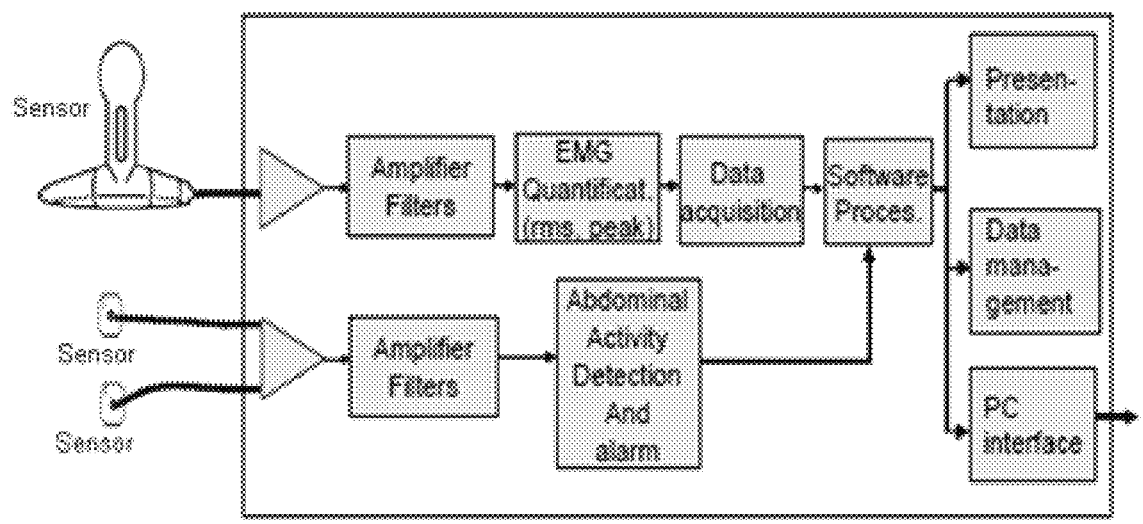
FIG. 1 shows by way of example a block diagram of the equipment for implementing the method of this invention.

The invention is implemented in a preferred embodiment with a system or equipment comprising a compact portable device providing a biofeedback signal relating to training exercises performed by a user. The exercises are for strengthening muscles of the pelvic floor for the treatment of urinary incontinence. The system comprises a probe 10 for capturing the electromyographic (EMG) signal relating to the pelvic floor. The probe can be a vaginal or rectal probe. The system also includes a second channel recording the EMG relating to abdominal muscles from sensors such as electrodes 11 applied in the lower abdomen, to assure that the exercises are being correctly performed. The EMG signals from both sources are filtered and amplified and then processed for obtaining the level of muscle activity.

The information about muscle activity (pelvic floor and abdomen) can be presented by way of numbers, graphs, or by means of an acoustic signal. The equipment will generally include (for example, stored in a memory) a set of preprogrammed exercises which can be configured by medical personnel. The equipment offers the user guidance for performing the exercises so that she achieves a certain level of activation of the two measurement channels. All the data is stored in a history log which will be wirelessly transmitted to a PC so that medical personnel can consult it a posteriori with reports, statistics, etc. The data may also be remotely transmitted from where the patient is to the center where the medical personnel is.

Therefore, the portable system can also be connected to a personal computer. When it is connected to the personal computer:

stored data corresponding to the exercises already performed can be transferred wirelessly, new exercise sessions can be programmed, and signals being recorded with the system at that time can be captured in real time.

The most important features of the biofeedback equipment for training the pelvic floor in patients with urinary incontinence are:

the equipment collects EMG from two channels, the vagina and abdomen, such that it is capable of discerning actual activity of the pelvic floor from that of the abdomen (to assure correct performance of the exercises);

the portable/home equipment allows initial configuration by doctors/therapists for performing daily sessions for a specific time (several weeks);

the equipment is capable of evaluating "online" the performance of the exercises and the levels of contraction achieved to increase the setpoint levels requested of the patient in the next exercises to be performed, facilitating patient progress and/or improvement;

not only does the portable equipment offer visual/acoustic feedback of the exercise being performed, but it also stores data relating to the exercises performed.

After an established home rehabilitation time, the portable equipment dumps the data into a computer, for example, a computer in a rehabilitation center, so that statistics are generated based on the variables of interest from the EMG signals, and clinical reports are prepared for the doctors which allows assessing patient progression. This information transfer could be done remotely, allowing remote patient care.

The equipment also measures muscle tone, using to that end sensors applied in the lower abdominal area, so that the level of contraction which the patients perform during exercises can subsequently be better assessed.

The portable equipment is capable of checking or verifying (assessing the signal received from the sensors) the correct placement of the sensors (for example, electrodes) and the vaginal probe.

FIG. 1 shows the components of the equipment and the steps of processing the captured EMG signals.

Figure 2:
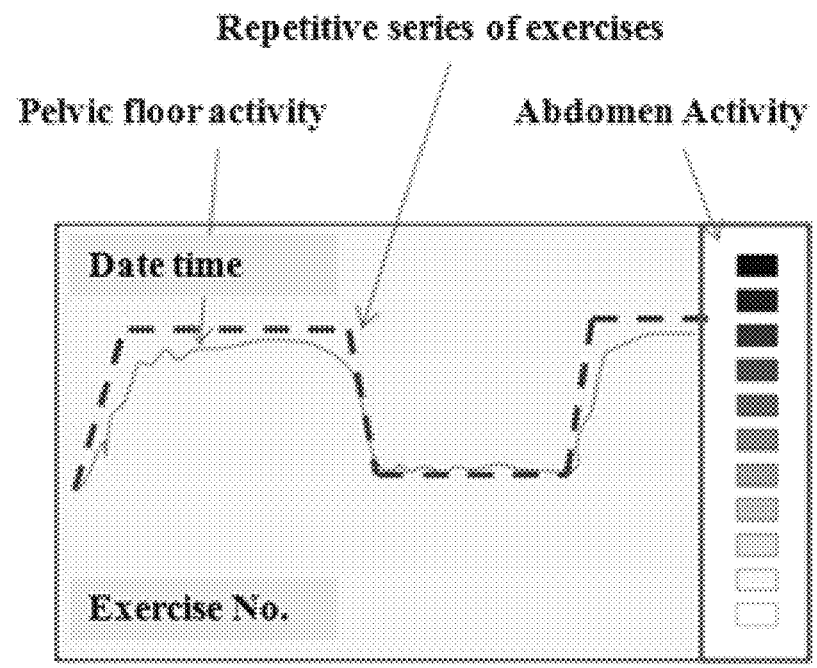
FIG. 2 illustrates a screen of the mentioned biofeedback equipment.

FIG. 2 illustrates an example of a display screen indicating the parameters shown to a user. In this example, the activity of the muscles of the pelvic floor (continuous line) is graphically shown together with the screen indicating the exercise to be performed (discontinuous line). The bar on the right simultaneously shows the activity of the abdominal muscles.

Figure 3:
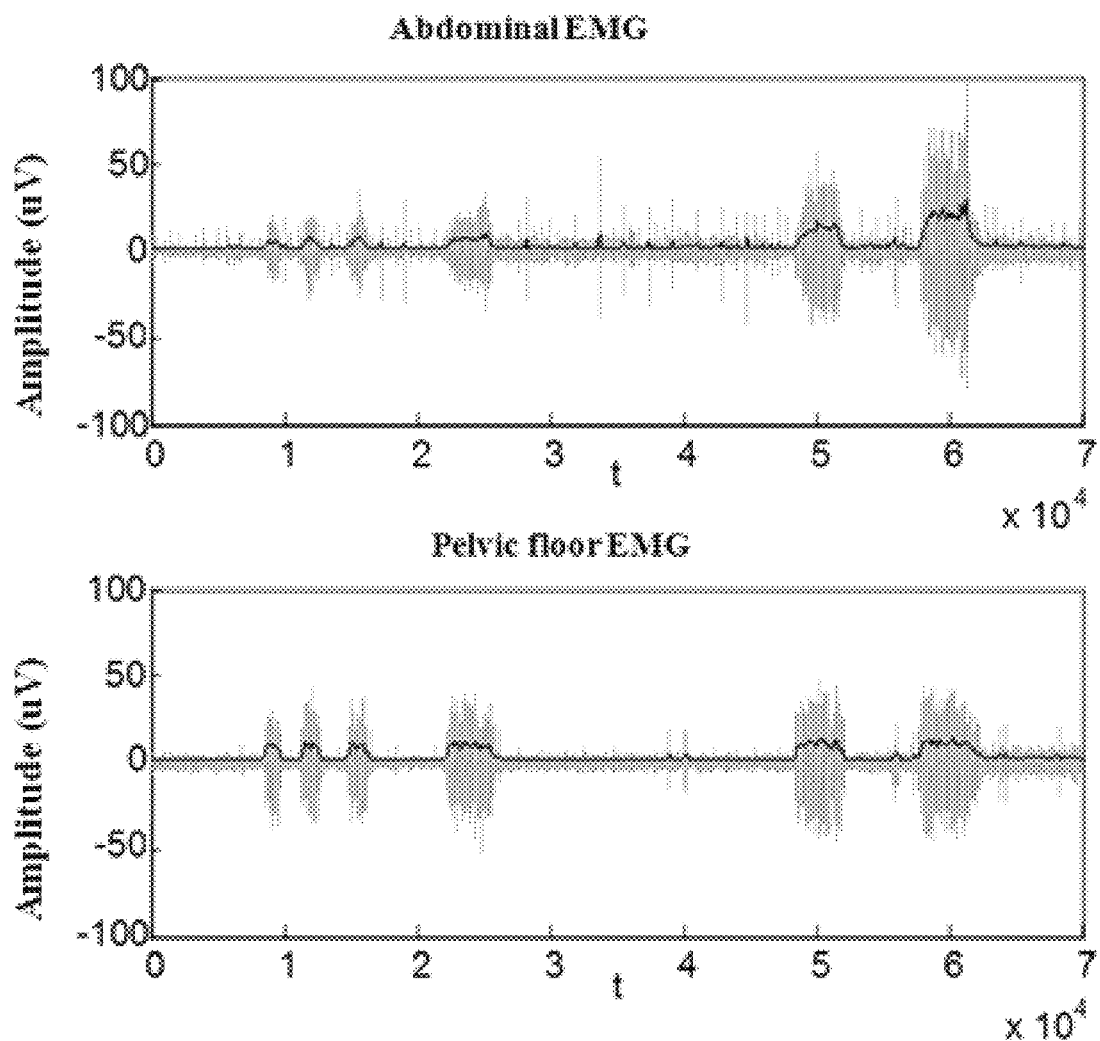
FIG. 3 shows in detail graphs with examples of EMG signals recorded in the pelvic floor and the abdomen and the result of processing said signals.

As indicated, FIG. 3 shows graphs with examples of EMG signals recorded in the pelvic floor and in the abdomen and the result of processing such signals.

The invention claimed is:

1. A method with biofeedback for training muscles of a pelvic floor, applicable to a treatment of urinary or fecal incontinence, the method comprising using a portable electronic device including a probe for capturing EMG signals relating to the pelvic floor, at least two sensors including electrodes for capturing EMG signals in a lower abdominal area, and a visual and/or an acoustic interface, by:

a) placing by a user herself in the user's vagina or rectum the probe;

b) placing by the user herself in the lower abdominal area said at least two sensors;

c) verifying a correct placement of the probe and of the at least two sensors indicating to the user that a suitable position has been reached through said visual and/or acoustic interface;

d) capturing the EMG signals relating to the pelvic floor and the EMG signals relating to abdominal muscles while the user performs a repetitive series of exercises;

e) filtering and amplifying both EMG signals relating to the pelvic floor and relating to abdominal muscles for obtaining, in real time, a level of muscle activity;

f) providing evaluations of the repetitive series of exercises to the user, while the user performs the repetitive series of exercises, via said visual and/or acoustic interface, simultaneously showing an activity of the muscles of the pelvic floor and of the lower abdominal area; and g) storing results of each session, wherein the method being performed after a training period, so parameters to be taken into account being adapted to conditions of the user for performing the exercises and to individual characteristics of the user, and wherein said verification of the correct placement of the probe and of said at least two sensors comprises measuring the captured EMG signals and comparing the EMG signals with threshold values sufficient for assessing a baseline muscle tone measurement, in response to a relaxation exercise, derived from the probe and of said at least two sensors, and emitting a visual confirmation, an acoustic confirmation or a repositioning request signal after measuring and evaluating a captured signal relating to abdominal activity.

2. The method according to claim 1, comprising performing first relaxation exercises before the user performing said repetitive series of exercises to establish a baseline level of muscle activity from a muscle tone captured by the EMG signals provided by said at least two sensors, and a maximum level, requesting to that end maximum contraction of said lower abdominal area from said user.

3. The method according to claim 1, wherein during the performing of said repetitive series of exercises a maximum number of repetitive and sustained or resistance contraction exercises are acquired, which the user is capable of performing, by repetition of a contraction exercise intended for training different types of muscle fibers of pelvic muscles.

4. The method according to claim 3, wherein during the performing of said repetitive series of exercises at least one maximum contraction of muscles of the pelvic floor or adjacent areas is requested.

5. The method according to claim 1, wherein results of the repetitive series of exercises performed in each session are stored in the portable electronic device, in a history log, for a next workout, and wherein parameters of said repetitive series of exercises are reconfigured for said next workout in a new session depending on said stored results and on a response of the correct placement verification.

6. The method according to claim 1, wherein said repositioning information is carried out with aid of the visual interface showing an image of the lower abdominal area on which areas where the at least two sensors must be placed are graphically illustrated.

7. The method according to claim 1, wherein the EMG signals captured by the probe and the EMG signals captured by the at least two sensors are wirelessly transmitted to said portable electronic device, including a radiofrequency transmission.

8. The method according to claim 7, wherein both said EMG signals are stored in said portable electronic device and later transmitted to a computer of a rehabilitation center for preparing clinical reports for evaluating and monitoring remote therapy compliance.

* * * * *